(12) United States Patent
Brook et al.

(10) Patent No.: US 7,666,857 B2
(45) Date of Patent: Feb. 23, 2010

US007666857B2

(54) 2-(3,4-DIMETHYLPHENYL)-4-{[2-HYDROXY-3'-(1H-TETRAZOL-5-YL)BIPHENYL-3-YL]-HYDRAZONO}-5-METHYL-2,4-DIHYDROPYRAZOL-3-ONE CHOLINE

(75) Inventors: Christopher S. Brook, King of Prussia, PA (US); Li-Jen J. Ping, King of Prussia, PA (US)

(73) Assignee: SmithKline Beecham Corp., Philadelphia, PA (US)

( * ) Notice: Subject to any disclaimer, the term of this patent is extended or adjusted under 35 U.S.C. 154(b) by 543 days.

(21) Appl. No.: 10/576,411

(22) PCT Filed: Oct. 21, 2004

(86) PCT No.: PCT/US2004/034944

§ 371 (c)(1),
(2), (4) Date: Apr. 20, 2006

(87) PCT Pub. No.: WO2005/041867

PCT Pub. Date: May 12, 2005

(65) Prior Publication Data

US 2007/0072922 A1    Mar. 29, 2007

(51) Int. Cl.
*C07D 403/12*    (2006.01)
*A61K 31/41*    (2006.01)
*A61K 31/655*    (2006.01)
*A61P 7/00*    (2006.01)

(52) U.S. Cl. .................. 514/150; 514/381; 534/775; 548/253

(58) Field of Classification Search .......... None
See application file for complete search history.

(56) References Cited

U.S. PATENT DOCUMENTS

| 851,444 | A | 4/1907 | Shulthess |
| 2,950,273 | A | 8/1960 | Pelz |
| 3,366,619 | A | 1/1968 | DeLucia |
| 4,435,417 | A | 3/1984 | Toja et al. |
| 4,510,149 | A | 4/1985 | Cozzi et al. |
| 4,880,788 | A | 11/1989 | Moake et al. |
| 4,948,900 | A | 8/1990 | Iijima et al. |
| 5,326,776 | A | 7/1994 | Winn et al. |
| 5,482,546 | A | 1/1996 | Eida et al. |
| 5,532,202 | A | 7/1996 | Yoshida |
| 5,622,818 | A | 4/1997 | Kapp et al. |
| 5,669,967 | A | 9/1997 | Hays |
| 5,746,821 | A | 5/1998 | Hays |
| 5,760,038 | A | 6/1998 | Murugesan et al. |
| 5,932,546 | A | 8/1999 | Barrett et al. |
| 6,214,813 | B1 | 4/2001 | Zhang et al. |
| 6,238,442 | B1 | 5/2001 | Schumacher et al. |
| 6,248,871 | B1 | 6/2001 | Ebenezer et al. |
| 6,280,959 | B1 | 8/2001 | Gleason et al. |
| 6,436,915 | B1 | 8/2002 | Zhang et al. |
| 2003/0060453 | A1 | 3/2003 | Zhang et al. |
| 2004/0063764 | A1 | 4/2004 | Takemoto et al. |
| 2004/0082626 | A1 | 4/2004 | Takemoto et al. |
| 2007/0105824 | A1 | 5/2007 | Erickson-Miller et al. |

FOREIGN PATENT DOCUMENTS

| DE | 193350 | 11/1904 |
| EP | 0 638 617 | 8/1994 |
| EP | 1 207 155 | 7/2000 |
| EP | 1 253 142 | 1/2001 |
| EP | 1 104 674 | 6/2001 |
| GB | 826207 | 7/1956 |
| GB | 779 880 | 7/1957 |
| JP | 2002-371213 | 12/2002 |
| WO | WO 93/17681 | 9/1993 |
| WO | WO 94/26709 | 11/1994 |
| WO | WO 96/40750 | 12/1996 |
| WO | WO 98/46606 | 10/1998 |
| WO | WO 99/11262 | 3/1999 |
| WO | WO 99/15500 | 4/1999 |
| WO | WO 00/35446 | 6/2000 |
| WO | WO 01/77080 | 1/2001 |
| WO | WO 01/07423 | 2/2001 |
| WO | WO 01/17349 | 3/2001 |
| WO | WO 01/21180 | 3/2001 |
| WO | WO 01/34585 | 5/2001 |
| WO | WO 01/89457 | * 11/2001 |
| WO | WO 02/59099 | 1/2002 |
| WO | WO 02/59100 | 1/2002 |
| WO | WO 02/49413 | 6/2002 |
| WO | WO 02/057300 | 7/2002 |
| WO | WO 02/085343 | 10/2002 |
| WO | WO 03/045379 | 6/2003 |
| WO | WO03/074550 | 9/2003 |
| WO | WO03/098992 | 12/2003 |
| WO | WO 03/103686 | 12/2003 |
| WO | WO 2004/054515 | 7/2004 |
| WO | WO 2005/041867 | 5/2005 |

OTHER PUBLICATIONS

Berge et al., "Pharmaceutical Salts", Journal of Pharmaceutical Sciences, 66(1), 1-18, 1977.*
Meade et al., "Biochemical Pharmacology of Platelet-Acitvating Factor (and PAF Antagonists) in Relation to Clinical and Experimental Thrombocytopenia", Biochemical Pharmacology, 41(5), 657-668, 1991.*
Gimenez et al., "Effect of CDP-Choline Administration on Brain Striatum Platelet-Activating Factor in Aging Rats", European Journal of Pharmacology, 344(⅔), 149-152, 1998.*
Yilmaz et al., "Intravenous Administration of Choline or CDP-Choline Improves Platelet Count and Platelet Closure Times in Endotoxin-Treated Dogs", Shock, 25(1), 73-79, 2006.*

(Continued)

*Primary Examiner*—Fiona T Powers
(74) *Attorney, Agent, or Firm*—Wayne J. Dustman; Edward R. Gimmi; Charles M. Kinzig

(57) ABSTRACT

An improved thrombopoietin mimetic, the choline salt of 2-(3,4-dimethylphenyl)-4-{[2-hydroxy-3'-(1H-tetrazol-5-yl)biphenyl-3-yl]-hydrazono}-5-methyl-2,4-dihydropyrazol-3-one.

21 Claims, 1 Drawing Sheet

OTHER PUBLICATIONS

Yamazaki, et al., Database HCAPLUS, AN 1995: Abstract, 196968.
A. Esteve, Ann. Pharm. Franc., 1950, vol. 8, No. 9-10, pp. 594-604.
Morris, et al., Anti-Cancer Drugs, 1997, vol. 8, No. 8, pp. 746-755.
Bartley, et al., Cell, 1994, vol. 77, pp. 1117-1124.
Olszewski, et al., Database CAPLUS on STN, 1995, Chem. Abstracts, No. 122:81695.
Olszewski, et al., J. Org. Chem., 1994, vol. 59, pp. 4285-4296.
Lamb, et al., Nucleic Acids Research, 1995, vol. 23, No. 16, pp. 3283-3289.
Seidel, et al., Proc. Natl. Acad. Sci. USA, Mar. 1995, vol. 92, pp. 3041-3045.
Berkhout, et al., J. of Biological Chemistry, Jun. 1997, vol. 272, No. 26, pp. 16404-16413.
Vermeulen, et al., Blood, 1998, vol. 92, No. 3, pp. 894-900.
Hasegawa, et al., Int. J. Immunopharmac, 1996, vol. 18, No. 2, pp. 103-112.
Kumamoto, et al., British Journal of Haematology, 1999, vol. 105, pp. 1025-1033.
Shiotsu, et al., Experimental Hematology, 1998, vol. 26, pp. 1195-1201.
Komatsu, et al., Blood, 1996, vol. 87, No. 11, pp. 4552-4560.
Uguccioni, et al., J. Exp. Med., 1996, vol. 183, pp. 2397-2384.
Taylor, et al., J. Org. Chem., 1987, vol. 52, pp. 4107-4110.
Kuter, et al., Seminars in Hematology, Apr. 2000, vol. 37, No. 2, pp. 41-49.
Ballestrero, et al., Oncology, 2000, vol. 59, pp. 7-13.
Sawai, et al., Journal of Leukocyte Biology, Jul. 2000, vol. 68, pp. 137-143.
Vigon, et al., Proc. Natl. Acad. Sci. USA, Jun. 1992, vol. 89, pp. 5640-5644.
Laurenz, et al., Comp. Biochem Physiol., 1997, vol. 116A, No. 4, pp. 369-377.
Metcalf, et al., Nature, Jun. 16, 1994, vol. 369, pp. 519-520.
Bussel, et al., Seminars in Hematology, 2000, vol. 37, pp. 1-49 (Table of Contents).
McDonald, et al., Am. J. of Pediatric Hematology/Oncology, 1992, vol. 14, No. 1, pp. 8-21.
Souyri, et al., Cell, 1990, vol. 63, pp. 1137-1147.
Bazan, et al., Pro. Natl. Acad. Sci. USA, Sep. 1990, vol. 87, pp. 6934-6938.
Sauvage, et al., Nature, Jun. 16, 1994, vol. 369, pp. 533-538.
Wendling, et al., Nature, Jun. 16, 1994, vol. 369, pp. 571-574.
Kaushansky, et al., Nature, Jun. 16, 1994, vol. 369, pp. 568-571.
King, et al., The Journal of Immunology, 2000, pp. 3774-3782.
Kikuta, et al., Experimental Hematology, 2000, vol. 28, pp. 311-317.
Somlo, et al., Blood, May 1, 1992, vol. 93, No. 9, pp. 2798-2806, 1999.
Kirley-Neumann, et al., Cytokines, Cellular & Molecular Therapy, 2000, vol. 6, pp. 47-56.
Egger, et al., Bone Marrow Transplant, 1998, vol. 22, pp. 34-35.
Gaudron, et al., Stem Cells, 1999, vol. 17, pp. 100-106.
Fetscher, et al., Current Opinion in Hematology, 2000, vol. 7, pp. 255-260.
Clemons, et al., Breast Cancer Res. Treatment, 1999, vol. 57, pp. 127.
Greene, "Protective Groups in Organic Synthesis", 1981, Table of Contents.
Methia, et al., Blood, 1993, vol. 82, No. 5, pp. 1395-1401.
Yamazaki, et al., Japn. J. Toxicol. Environ. Health, 1994, vol. 94, No. 5, pp. 448-453.
Duffin, et al., J. of the Chem. Soc., 1954, pp. 408-441.
King, et al., Scand. J. of Immunol., 1999, vol. 49, No. 2, pp. 184-192.
Konica Corp. Derwent No. 92-077508/10, 1992.
Mitsubishi Pharma Corp. Derwent No. 2003-845201/78, 2003.
Mitsubishi Pharma Corp. Derwent No. 2003-767492/72, 2003.
Balli, et al., Dyes. Pigm., 1981, vol. 2, No. 2, pp. 93-124.
Balli, et al., Justus Liebigs Ann. Chem., 1966, vol. 699, pp. 133-134.
Dziomko, et al., Chem. Heterocycl. Compd., 1984, vol. 20, No. 2, pp. 196-200.
Duffy, et al., J. Med. Chem., 2001, vol. 44, No. 22, p. 3730-3745.
Kimura, et al., FEBS Letters, 1998, vol. 428, No. 3, pp. 250-254.
Beckert, et al., Monatshefte Fur Chemie, 1989, vol. 120, pp. 1125-1137.
A. Esteve, Ann. Pharm. Franc., 1950, vol. 8, No. 9-10.
Minssen-Guette, et al., Bulletin De La Societe Chimique De France, 1968, No. 5, pp. 2106-2110.
European Search report dated Dec. 15, 2003.
European office action dated Feb. 2, 2005.
Bussel, et al., Seminars in Hematology, 2000, vol. 37, pp. 1-49 (whole journal).

* cited by examiner

2-(3,4-DIMETHYLPHENYL)-4-{[2-HYDROXY-3'-(1H-TETRAZOL-5-YL)BIPHENYL-3-YL]-HYDRAZONO}-5-METHYL-2,4-DIHYDROPYRAZOL-3-ONE CHOLINE

This application claims the benefit of U.S. Provisional Application No. 60/513,481, filed Oct. 22, 2003.

This invention relates to an improved thrombopoietin (hereinafter TPO)mimetic, the choline salt of 2-(3,4-dimethylphenyl)-4-{[2-hydroxy-3'-(1H-tetrazol-5-yl)biphenyl-3-yl]-phydrazono}-5-methyl-2,4-dihydropyrazol-3-one. The compound is represented by Structure I:

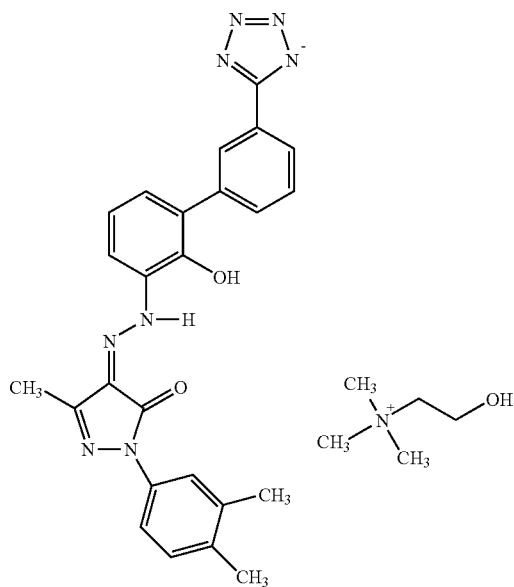

(I)

The compound of this invention is useful as an agonist of the TPO receptor, particularly in enhancing platelet production.

Figure 1:
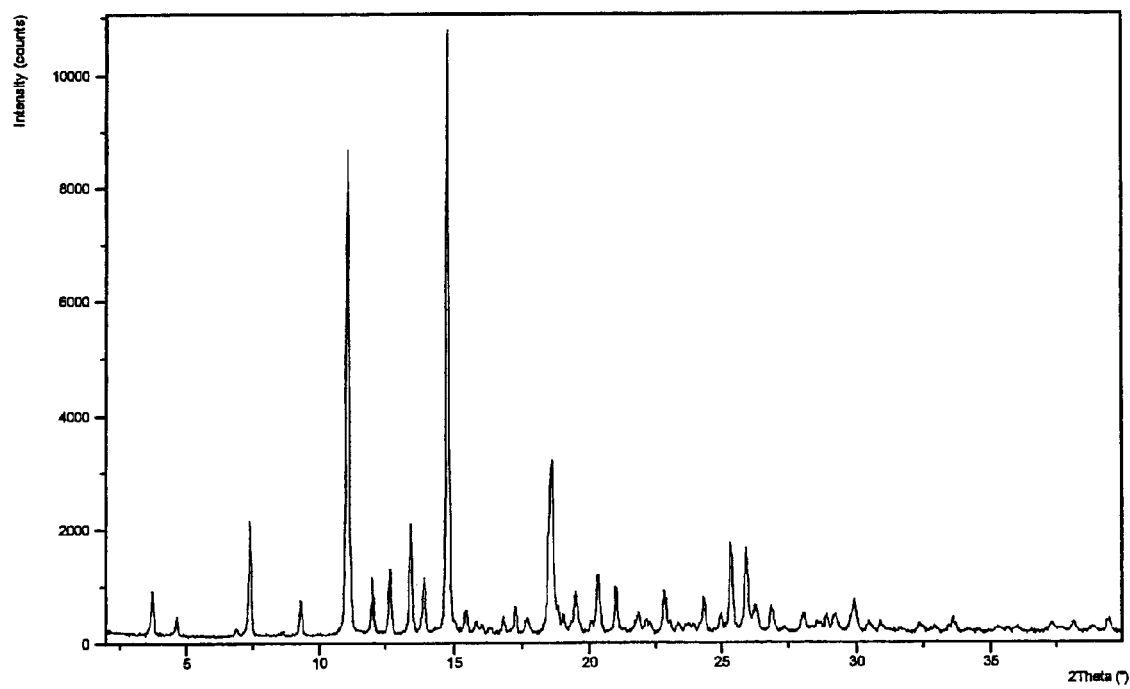
FIG. 1 depicts an X-ray powder diffraction pattern of 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline.

DETAILED DESCRIPTION OF THE INVENTION 2-(3,4-dimethylphenyl)-4-{[2-hydroxy-3'-(1H-tetrazol-5-yl)biphenyl-3-yl]-hydrazono}-5-methyl-2,4-dihydropyrazol-3-one is a compound which is disclosed and claimed, along with pharmaceutically acceptable salts, hydrates, solvates and esters thereof, as being useful as an agonist of the TPO receptor, particularly in enhancing platelet production and particularly in the treatment of thrombocytopenia, in International Application No. PCT/US01/16863, having an International filing date of May 24, 2001; International Publication Number WO 01/89457 and an International Publication date of Nov. 29, 2001 (compound of Example 12), the entire disclosure of which is hereby incorporated by reference. International Application No. PCT/US01/16863 does not specifically disclose a salt form for any of the compounds disclosed therein.

It has now surprisingly been found that the choline salt of 2-(3,4-dimethylphenyl)-4-{[2-hydroxy-3'-(1H-tetrazol-5-yl)biphenyl-3-yl]-hydrazono}-5-methyl-2,4-dihydropyrazol-3-one has numerous advantages over the free acid. The free acid is poorly soluble in water. This poor solubility adversely affects the ability of the free acid to be formulated into pharmaceutical dosage forms and reduces the bioavailability and oral exposure of the compound in vivo.

While the free acid is highly useful as an agonist of the TPO receptor, particularly in enhancing platelet production and particularly in the treatment of thrombocytopenia, the choline salt of 2-(3,4-dimethylphenyl)-4-{[2-hydroxy-3'-(1H-tetrazol-5-yl)biphenyl-3-yl]-hydrazono}-5-methyl-2,4-dihydropyrazol-3-one has the added advantages of enhanced bioavailability and oral exposure.

The compound of this invention, 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline (hereinafter—"Active Ingredient" or "Compound A"), is useful as an agonist of the TPO receptor, particularly in enhancing platelet production and particularly in the treatment of thrombocytopenia. The Active Ingredient can be administered in a conventional dosage form prepared by combining the Active Ingredient with a conventional pharmaceutically acceptable carrier or diluent according to techniques readily known to those of skill in the art, such as those described in International Application No. PCT/US01/16863.

Suitably, the present invention includes within its scope pharmaceutical compositions comprising 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline, as the Active Ingredient, in association with a pharmaceutically acceptable carrier or diluent. Compound A of this invention can be administered by oral, parenteral, intradermal or topical routes of administration. The term parenteral as used herein includes intravenous, intramuscular, subcutaneous, intranasal, intrarectal, intravaginal and intraperitoneal administration. Oral administration is generally preferred. Compound A can be formulated in dosage forms appropriate for each route of administration including capsules, tablets, pills, powders and granules. In such solid dosage forms, the active compound is generally admixed with at least one inert diluent. The oral dosage forms can also comprise, as is normal practice, additional substances other than inert diluents, e.g., lubricating agents, glidants and antioxidants. In the case of capsules, tablets and pills, the dosage forms may also comprise buffering agents. Tablets and pills can additionally be prepared for a sustained release.

Preparations according to this invention for parenteral administration include sterile aqueous solutions although nonaqueous suspensions of emulsions can be employed. Such dosage forms may also contain adjuvants such as preserving, wetting, osmotic, buffering, emulsifying and dispersing agents. They may be sterilized by, for example, filtration through a bacteria retaining filter, by incorporating sterilizing agents into the compositions, irradiating the compositions or by heating the compositions.

As used herein "choline" means (2-hydroxyethyl)trimethylammonium.

Doses of the presently invented Active Ingredient in a pharmaceutical dosage unit as described above will be an efficacious, nontoxic quantity preferably selected from the range of 0.001-100 mg/kg of total body weight, preferably 0.001-50 mg/kg. When treating a human patient in need of a TPO mimetic, the selected dose is preferably administered from 1-6 times daily, orally or parenterally. Preferred forms of parenteral administration include topically, rectally, transdermally, by injection and continuously by infusion. Oral dosage units for human administration preferably contain from 0.05 to 3500 mg of Active Ingredient, most preferably from 0.5 to 1,000 mg of Active Ingredient. Oral administration, which uses lower dosages is preferred. Parenteral administration, at high dosages, however, also can be used when safe and convenient for the patient. The above dosages relate to the preferred amount of the Active Ingredient expressed as the free acid.

It will be recognized by one of skill in the art that the optimal quantity and spacing of individual dosages of the Active Ingredient will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the Active Ingredient given per day for a defined number of days, can be ascertained by those skilled in the art using conventional course of treatment determination tests.

Generally speaking, the compound of this invention is prepared by dissolving the free acid, 2-(3,4-dimethylphenyl)-4-{[2-hydroxy-3'-(1H-tetrazol-5-yl)biphenyl-3-yl]-hydrazono}-5-methyl-2,4-dihydropyrazol-3-one, in an appropriate organic solvent, such as a mixture of ethanol and ethyl acetate, filtering the resultant mixture to remove contaminants, then adding this solution to a solution of, for example, 1.5 equivalents of choline hydroxide in an organic solvent, preferably a water-miscible solvent, such as MeOH or THF. The compound of this invention is precipitated out, generally over 3 to 24 hours, then is filtered off and dried, for example, dried in vacuo or air dried at an elevated temperature.

Choline hydroxide 50 wt. % solution in methanol, was purchased from the Aldrich Chemical Company, Milwaukee, Wis.

Organic solvents are available from the Aldrich Chemical Company, Milwaukee, Wis.

Because the pharmaceutically active compound of the present invention is active as a TPO mimetic it exhibits therapeutic utility in treating thrombocytopenia and other conditions with depressed platelet production.

The treatment of thrombocytopenia, as described herein, is accomplished by increasing the production of platelets.

By the term "thrombocytopenia" and derivatives thereof as used herein is to be broadly interpreted as any decrease in the number of blood platelets below what is considered normal or desired for a healthy individual. Thrombocytopenia is known to have many causative factors, including but not limited to, radiation therapy, chemotherapy, immune therapy, immune thrombocytopenic purpura (ITP, Bussel J. B., *Seminars in Hematology*, 2000, 37, Suppl 1, 1-49), myelodysplastic syndrome (MDS), aplastic anemia, AML, CML, viral infections (including, but not limited to; HIV, hepatitis C, parvovirus) liver disease, myeloablation, bone marrow transplant, stem cell transplant, peripheral blood stem cell transplant, progenitor cell defect, polymorphisms in stem cells and progenitor cells, defects in Tpo, neutropenia (Sawai, N. *J. Leukocyte Biol.*, 2000, 68, 137-43), dendritic cell mobilization (Kuter D. J. *Seminars in Hematology*, 2000, 37, Suppl 4, 41-49), proliferation, activation or differentiation. The pharmaceutically active compound of this invention is useful in treating thrombocytopenia regardless of the factor or factors causing the condition. The pharmaceutically active compound of this invention is also useful in treating thrombocytopenia when the causative factor or factors of the condition are unknown or have yet to be identified.

TPO has been demonstrated to act as a mobilizer of stem cells into the peripheral blood (Neumann T. A. et al., *Cytokines, Cell. & Mol. Ther.*, 2000, 6, 47-56). This activity can synergize with stem cell mobilizers such as G-CSF (Somolo et al., *Blood*, 1999, 93, 2798-2806). The compound of the present invention is thus useful in increasing the numbers of stem cells in circulation in donors prior to leukapheresis for hematopoietic stem-cell transplantation in patients receiving myeloablative chemotherapy.

Likewise, TPO stimulates growth of myeloid cells, particularly those of granulocyte/macrophage lineage (Holly et al., U.S. Pat. No. 5,989,537). Granulocyte/macrophage progenitors are cells of the myeloid lineage that mature as neutrophils, monocytes, basophils and eosinophils. The compound of the present invention thus has therapeutic utility in stimulating the poliferation of neutrophils in patients with neutropenic conditions.

Prophylactic use of the compound of this invention is contemplated whenever a decrease in blood or blood platelets is anticipated. Prophylactic use of Compound A results in a build up of platelets or a commencement of platelet production prior to an anticipated loss of blood or blood platelets. Prophylactic uses of Compound A includes but is not limited to transplant surgery, surgery, anesthesia prior to child birth and gut protection.

Human dendritic cells have been shown to express the TPO receptor (Kumamoto et al., *Br. J. Haem*, 1999, 105, 1025-1033) and TPO is a potent mobilizer of dendritic cells. The TPO mimetic compound of the current invention is also useful as a vaccine adjuvant in that it increases the activity and mobility of dendritic cells. Compound A is useful as an immunological adjuvant, given in combination with an orally, transdermally or subcutaneously delivered vaccine and/or immunomodulator, by increasing the activity and mobility of dendritic cells.

TPO is known to have various effects including anti-apototic/survival effects on megakaryocytes, platelets and stem cells, and proliferative effects on stem cells and megakaryocytic cells (Kuter D. J. Seminars in Hematology, 2000, 37, 41-9). These TPO activities effectively increase the number of stem and progenitor cells so that there are synergistic effects when TPO is used in conjunction with other cytokines that induce differentiation.

A further aspect of the invention provides for a method of treating degenerative diseases in a mammal, including a human, in need thereof which comprises administering to such mammal a therapeutically effective amount of presently invented Compound A.

By the term degenerative disease, and derivatives thereof, as used herein is meant a disease state selected from: nervous system disorders, including transverse myelitis, multiple sclerosis, demyelination occurring after trauma to the brain or spinal cord, acute brain injury, head trauma, peripheral nerve injury, ischaemic brain injury, spinal cord injury, hereditary myelin disorder of the CNS, epilepsy, perinatal asphyxia, asphyxia, anoxia, status epilepticus, and stroke; neurodegenerative diseases such as Alzheimer's disease, Parkinson disease, Huntington's disease, and amyotrophic lateral sclerosis; in the treatment, repair and/or regeneration of tissue, for example: in cardiovascular disorders, myocardial infarction and cardiovascular disease/tissue, and in the treatment, repair and/or regeneration of liver disease/tissue, gastrointestinal disease/tissue and kidney disease/tissue; in the treatment of AIDS; and in the treatment of diabetes/diabetes mellitus.

Stroke refers to a cerebral vascular incident (CVI) and includes acute thromboembolic stroke. Stroke includes both focal and global ischemia. Also included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension, as well as similar injuries seen during procedures from embole, hyperfusion, and hypoxia.

Compound A is useful in a range of incidents, for example, during cardiac bypass surgery, in incidents of intracranial hemorrhage, in perinatal asphyxia, in cardiac arrest, and status epilepticus.

The present invention therefore provides a method of treating a disease state selected from: nervous system disorders, including transverse myelitis, multiple sclerosis, demyelination occurring after trauma to the brain or spinal cord, acute brain injury, head trauma, spinal cord injury, peripheral nerve injury, ischaemic brain injury, hereditary myelin disorder of the CNS, epilepsy, perinatal asphxia, asphyxia, anoxia, status epilepticus, and stroke; neurodegenerative diseases such as Alzheimer's disease, Parkinson disease, Huntington's disease, and amyotrophic lateral sclerosis; in the treatment, repair and/or regeneration of tissue, for example: in cardiovascular disorders, myocardial infarction and cardiovascular disease/tissue, and in the treatment, repair and/or regeneration of liver disease/tissue, gastrointestinal disease/tissue and kidney disease/tissue; in the treatment of AIDS; and in the treatment of diabetes/diabetes mellitus which comprises the administration an effective amount of Compound A.

The treatment of degenerative diseases, as described herein, is accomplished by the administration of Compound A and is not limited to any particular mechanism of action. A mechanism of action for treating the degenerative diseases, as described herein, is by stimulating the survival and/or production of stem cells and/or increasing stem cell function and/or longevity.

Degenerative diseases are known to have many causative factors, including but not limited to, viral infections (including, but not limited to; HIV, hepatitis C, parvovirus) and liver disease, aging, auto immune diseases, neural disease/damage, liver disease/damage, kidney disease/damage, gastrointestinal disease/damage, cardiovascular disease/damage and pancreatic disease/damage. This invention relates to the treatment of degenerative diseases regardless of the factor or factors causing the condition. The compound of this invention, Compound A, is also useful in treating degenerative diseases when the causative factor or factors of the condition are unknown or have yet to be identified.

A skilled physician will be able to determine the appropriate situation in which subjects are susceptible to or at risk of a degenerative disease, for example, stroke as well as suffering from stroke for administration by methods of the present invention.

Prophylactic use of the compounds of this invention is contemplated whenever a degenerative disease is anticipated.

The ability of Compound A to treat degenerative diseases is demonstrated by activity in the CD34+ Progenitor Cell Proliferation Assay.

CD34+ Progenitor Cell Proliferation Assay

Compound A is tested for its ability in stimulating the survival and proliferation of early CD34+ progenitor cells from human bone marrow. In this assay, purified human CD34+ progenitor cells are incubated in liquid culture with Compound A for up to 7 days and the number of cells expressing the early stem cell marker CD34 is then measured by flow cytometry and compared to untreated cells (see Liu et al. Bone Marrow Transplantation. 24:247-52, 1999).

The present invention therefore provides a method of treating degenerative diseases, which comprises the administration an effective amount of Compound A to a subject in need thereof. Compound A provides for a method for treating the above indicated disease states because of its ability to treat degenerative diseases.

It is part of this discovery that the in vivo administration of Compound A is useful in treating Parkinson's disease, Huntingtion's disease, multiple sclerosis and ischaemic brain injury. Stem cells, including adult bone marrow stem cells are indicated as effective in treating multiple sclerosis; Stangel M. et al., *Progress in Neurobiology,* 68(5): 361-76, 2002 December Neural stem cells and their use in Parkinson's disease, Huntingtion's disease, multiple sclerosis and ischaemic brain injury is described in Ostenfield T. et al., *Advances & Technical standards in Neurosurgery,* 28: 3-89, 2003.

Further, it is part of this discovery that the in vivo administration of Compound A is useful in the regeneration and repair of tissues that respond to stem cell treatment. Such tissues are readily known or readily ascertainable by those skilled in the art. For example, stem cells are indicated as being useful in treating patients with myocardial infarction, cardiovascular disorders and cardiovascular disease; Stamm C. et al., *Lancet.* 361(9351): 45-6, 2003 and Semsarian C., *Internal Medicine Journal.* 32(5-6): 259-65, 2002. Stem cells are indicated in treating, repairing and/or in the regeneration of liver disease/tissue, gastrointestinal disease/tissue and kidney disease/tissue; Choi D. et al., *Cell transplantation,* 11(4): 359-68, 2002, Poulsom R. et al., *Journal of Pathology,* 197 (4): 441-56, 2002 and Alison M. et al., *Journal of Pathology,* 197 (4): 419-23, 2002.

Further, it is part of this discovery that the in vivo administration of Compound A is useful in the treatment of diabetes/diabetes mellitus. Stem cells are indicated in treating diabetes, Berna G, et al., *Biomedicine & Pharmacotherapy,* 55(4): 206-12, 2001 and Beilhack G F., et al., *Diabetes,* 52(1):59-68, 2003.

A further aspect of the invention provides for methods of co-administering the presently invented Compound A with further active ingredients, such as other compounds known to treat degenerative diseases and/or thrombocytopenia, including chemotherapy-induced thrombocytopenia and bone marrow transplantation and other conditions with depressed platelet production, or compounds known to have utility when used in combination with a TPO mimetic.

By the term "co-administering" and derivatives thereof as used herein is meant either simultaneous administration or any manner of separate sequential administration of Compound A, and a further active ingredient or ingredients, known to treat degenerative diseases and/or thrombocytopenia, including chemotherapy-induced thrombocytopenia and bone marrow transplantation and other conditions with depressed platelet production. The term further active ingredient or ingredients, as used herein, includes any compound or therapeutic agent known to have or that demonstrates advantageous properties when administered with TPO or a TPO mimetic. Preferably, if the administration is not simultaneous, the compounds are administered in a close time proximity to each other. Furthermore, it does not matter if the compounds are administered in the same dosage form, e.g. one compound may be administered topically and another compound may be administered orally.

The TPO mimetic compound of the current invention is also useful in acting on cells for survival or proliferation in conjunction with other agents known to act on cells for survival or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195-1201), uteroferrin (Laurenz J C., et al. *Comp. Biochem. & Phys., Part A. Physiology.,* 1997, 116, 369-77), FK23 (Hasegawa T., et al. *Int. J. Immunopharm.,* 1996, 18 103-112) and other molecules identified as having anti-apoptotic, survival or proliferative properties for stem cells, progenitor cells, or other cells expressing Tpo Receptors.

Examples of a further active ingredient or ingredients for use in combination with the presently invented Compound A include but are not limited to: chemoprotective or myeloprotective agents such as G-CSF, BB10010 (Clemons et al., *Breast Cancer Res. Treatment,* 1999, 57, 127), amifostine (Ethyol) (Fetscher et al., *Current Opinion in Hemat.,* 2000, 7, 255-60), SCF, IL-11, MCP-4, IL-1-beta, AcSDKP (Gaudron et al., *Stem Cells,* 1999, 17, 100-6), TNF-a, TGF-b, MIP-1a (Egger et al., *Bone Marrow Transpl.,* 1998, 22 (Suppl. 2), 34-35), and other molecules identified as having anti-apoptotic, survival or proliferative properties.

Additional examples of a further active ingredient or ingredients for use in combination with the presently invented TPO mimetic compound includes but is not limited to: stem cell, megakaryocyte, neutrophil mobilizers such as chemotherapeutic agents (i.e., cytoxan, etoposide, cisplatin, Ballestrero A. et al., *Oncology,* 2000, 59, 7-13), chemokines, IL-8, Grobeta (King, A. G. et al. *J. Immun.,* 2000, 164, 3774-82), receptor agonist or antagonist antibodies, small molecule cytokine or receptor agonists or antagonists, SCF, Flt3 ligand, adhesion molecule inhibitors or antibodies such as: anti-VLA-4 (Kikuta T. et al., *Exp. Hemat.,* 2000, 28, 311-7) or anti-CD44 (Vermeulen M. et al., *Blood,* 1998, 92, 894-900), cytokine/chemokine/interleukin or receptor agonist or antagonist antibodies, MCP-4 (Berkhout T A., et al., *J. Biol. Chem.,* 1997, 272, 16404-16413; Uguccioni M. et al., *J. Exp. Med.,* 1996, 183, 2379-2384).

Compound A of this invention is useful as a TPO mimetic in mammals, particularly humans, in need thereof.

The method of this invention of inducing TPO mimetic activity in mammals, including humans, comprises administering to a subject in need of such activity an effective TPO mimetic amount of Compound A of the present invention.

The invention also provides for the use of Compound A in the manufacture of a medicament for use in therapy.

The invention also provides for the use of Compound A in the manufacture of a medicament for use as a TPO mimetic.

The invention also provides for the use of Compound A in the manufacture of a medicament for use in enhancing platelet production.

The invention also provides for the use of Compound A in the manufacture of a medicament for use in treating thrombocytopenia.

The invention also provides for the use of Compound A in the manufacture of a medicament for use in the treatment of degenerative diseases.

The invention also provides for a pharmaceutical composition for use in the treatment of degenerative diseases which comprises Compound A and a pharmaceutically acceptable carrier.

The invention also provides for a pharmaceutical composition for use as a TPO mimetic which comprises Compound A and a pharmaceutically acceptable carrier.

The invention also provides for a pharmaceutical composition for use in the treatment of thrombocytopenia which comprises Compound A and a pharmaceutically acceptable carrier.

The invention also provides for a pharmaceutical composition for use in enhancing platelet production which comprises Compound A and a pharmaceutically acceptable carrier.

The invention also provides for a pharmaceutical composition for use in treating degenerative diseases which comprises Compound A and a pharmaceutically acceptable carrier.

By the term "treating" and derivatives thereof as used herein, is meant prophylatic and therapeutic therapy.

All publications, including but not limited to patents and patent applications, cited in this specification are herein incorporated by reference as though fully set forth.

No unacceptable toxicological effects are expected when the compound of the invention is administered in accordance with the present invention.

Contemplated Equivalents—It will be appreciated by the person of ordinary skill in the art that Compound A may also exist in tautomeric forms. Tautomeric forms of Compound A may include, but are not limited to, structures formally represented by the following formulae (II and III).

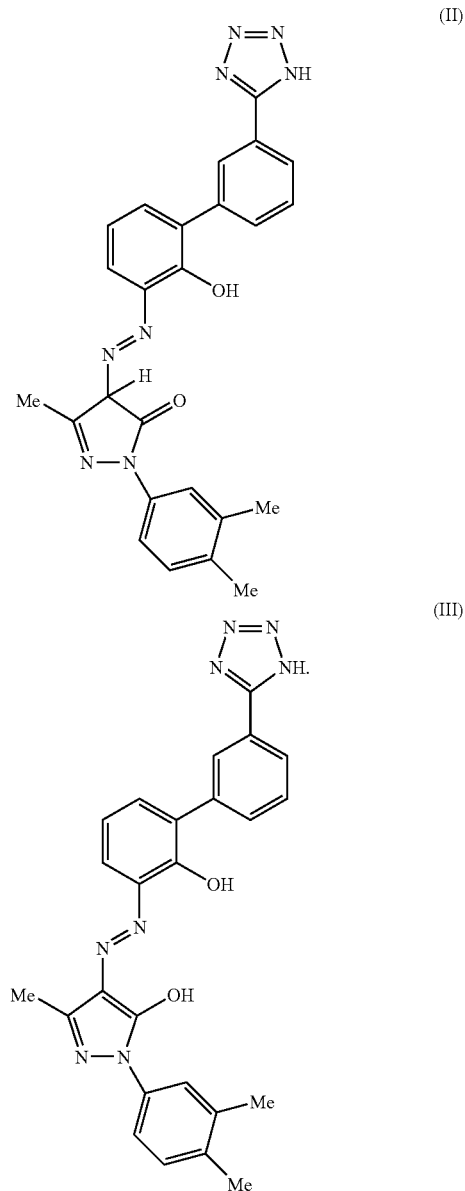

All such compounds are included in the scope of the invention and inherently included in the definition of Compound A.

The following examples further illustrate the present invention. The examples are not intended to limit the scope of the invention as defined hereinabove and as claimed below.

EXAMPLE 1

Preparation of 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline

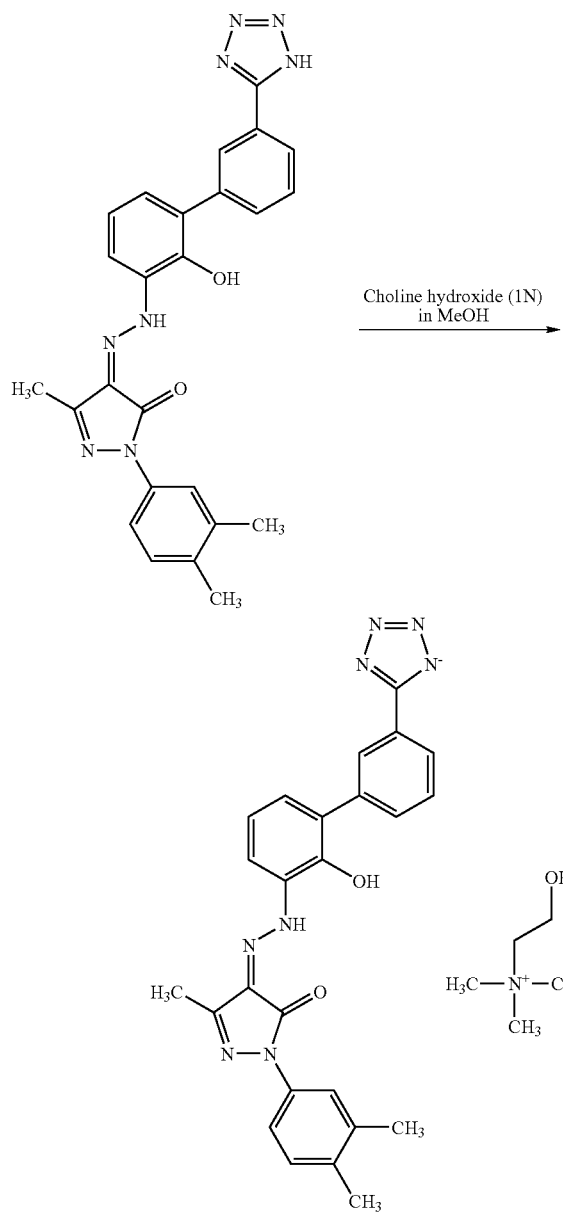

2-(3,4-Dimethylphenyl)-4-{[2-hydroxy-3'-(1H-tetrazol-5-yl)biphenyl-3-yl]-hydrazono}-5-methyl-2,4-dihydropyrazol-3-one, 1.1 g of crude orange solid, in 7 mL of ethyl acetate and 12 mL of ethanol (190 proof) was stirred at approximately 40° C. To this suspension 2.5 ml of choline hydroxide (1N) solution in methanol was added resulting in a dark orange brown solution. Water (1 ml) was added to the dark solution and the mixture stirred at approx. 35° C. for approx. 3 hours. During this time, precipitation was seen in the solution. The suspension was stirred for another 72 hours at approx. 20° C., and then the solid was isolated by filtration and dried at approx. 40° C. over 12 hours to yield 1.2 gram (87% yield) of the title compound as a crystalline solid with a light orange color.

The solid was proved to be crystalline by X-ray powder diffraction taken on a Philips X'Pert Pro diffractometer. The sample was scanned with the following parameters: scan range: 2-35 degrees two-theta; generator power: 40 kV, 40 mA; radiation source: Cu Kα; scan type: continuous; step time: 10.16 seconds; step size: 0.0167 degrees two-theta per step; sample rotation: 25 rpm. Following is an X-ray peak list. An X-ray powder pattern is depicted in FIG. 1.

| No. | Pos. [°2Th.] | d-spacing [Å] | Height [cts] | Rel. Int. [%] |
|---|---|---|---|---|
| 1 | 3.7251 | 23.71979 | 765.16 | 7.1 |
| 2 | 4.6611 | 18.95844 | 281.32 | 2.61 |
| 3 | 6.9016 | 12.80813 | 132.23 | 1.23 |
| 4 | 7.398 | 11.94973 | 1973.41 | 18.32 |
| 5 | 8.631 | 10.24525 | 79.49 | 0.74 |
| 6 | 9.2935 | 9.51632 | 591.28 | 5.49 |
| 7 | 11.0789 | 7.98639 | 8263.89 | 76.71 |
| 8 | 12.0073 | 7.37092 | 1010.77 | 9.38 |
| 9 | 12.6611 | 6.99174 | 1142.5 | 10.61 |
| 10 | 13.4261 | 6.59499 | 1954.15 | 18.14 |
| 11 | 13.9252 | 6.35974 | 935.82 | 8.69 |
| 12 | 14.7822 | 5.9929 | 10773.16 | 100 |
| 13 | 15.4472 | 5.73636 | 448.55 | 4.16 |
| 14 | 15.821 | 5.60168 | 247.91 | 2.3 |
| 15 | 16.0339 | 5.52779 | 187.08 | 1.74 |
| 16 | 16.3397 | 5.42501 | 133.42 | 1.24 |
| 17 | 16.827 | 5.26898 | 323.14 | 3 |
| 18 | 17.2645 | 5.13643 | 503.18 | 4.67 |
| 19 | 17.7 | 5.01104 | 303.14 | 2.81 |
| 20 | 18.4945 | 4.79752 | 1781.54 | 16.54 |
| 21 | 18.617 | 4.76623 | 3054.95 | 28.36 |
| 22 | 18.8171 | 4.71597 | 523.32 | 4.86 |
| 23 | 19.0441 | 4.66028 | 351.15 | 3.26 |
| 24 | 19.4943 | 4.55365 | 759.39 | 7.05 |
| 25 | 20.0493 | 4.42884 | 237.18 | 2.2 |
| 26 | 20.2993 | 4.37486 | 976.47 | 9.06 |
| 27 | 20.9924 | 4.23196 | 826.54 | 7.67 |
| 28 | 21.8349 | 4.07054 | 401.19 | 3.72 |
| 29 | 22.1116 | 4.02021 | 277.22 | 2.57 |
| 30 | 22.7938 | 3.90141 | 772.82 | 7.17 |
| 31 | 23.3318 | 3.81267 | 198.84 | 1.85 |
| 32 | 23.6942 | 3.75516 | 194.32 | 1.8 |
| 33 | 24.3066 | 3.66191 | 646.51 | 6 |
| 34 | 24.9588 | 3.56769 | 361.6 | 3.36 |
| 35 | 25.3337 | 3.51573 | 1565.54 | 14.53 |
| 36 | 25.8945 | 3.44085 | 1500.67 | 13.93 |
| 37 | 26.28 | 3.39125 | 464.38 | 4.31 |
| 38 | 26.8355 | 3.3223 | 491.62 | 4.56 |
| 39 | 28.0401 | 3.18225 | 379.9 | 3.53 |
| 40 | 28.8594 | 3.09375 | 323.9 | 3.01 |
| 41 | 29.1842 | 3.06005 | 347.59 | 3.23 |
| 42 | 29.9265 | 2.98582 | 615.82 | 5.72 |
| 43 | 30.4456 | 2.93608 | 205.95 | 1.91 |
| 44 | 30.887 | 2.89513 | 209.21 | 1.94 |
| 45 | 31.6721 | 2.82513 | 111.93 | 1.04 |
| 46 | 32.3596 | 2.76666 | 186.65 | 1.73 |
| 47 | 32.9388 | 2.71932 | 135.38 | 1.26 |
| 48 | 33.5777 | 2.66903 | 266.78 | 2.48 |
| 49 | 34.1496 | 2.62563 | 98.41 | 0.91 |
| 50 | 35.9386 | 2.49893 | 127 | 1.18 |
| 51 | 37.317 | 2.40973 | 197.26 | 1.83 |
| 52 | 38.1296 | 2.36023 | 208.09 | 1.93 |
| 53 | 38.8183 | 2.31992 | 140.58 | 1.3 |
| 54 | 39.4044 | 2.28676 | 240.8 | 2.24 |

DSC data showed the solid melts with decomposition with an endotherm onset at about 235.3° C.

Proton NMR (400 MHz, MeOH-d4 referenced to MeOH-d4 δ3.32): δ 2.28 (s, 3H), 2.31 (s, 3H), 2.39 (s, 3H), 3.21 (s, 9H), 3.47-3.49 (t, 2H), 3.99-4.01 (t, 2H), 7.10-7.13 (dd, 1H), 7.17-7.18 (d, 1H), 7.20-7.21 (dd, 1H), 7.55-7.60 (m, 3H), 7.68 (br. s, 1H), 7.76-7.77 (dd, 1H), 8.06-8.07 (dd, 1H), 8.21 (s, 1H) IR Data (DATR) 3023, 2920, 2853, 1648, 1606, 1541, 1503, 1457, 1410, 1367, 1334, 1267, 1257, 1224, 1191, 1155, 1135, 1117, 1097, 1054, 1024, 1000, 958, 920, 904, 874, 851, 806, 784, 773, 760, 726, 708, 681 cm$^{-1}$

EXAMPLE 2

Preparation of 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline 2-(3,4-Dimethylphenyl)-4-{[2-hydroxy-3'-(1H-tetrazol-5-yl)biphenyl-3-yl]-hydrazono}-5-methyl-2,4-dihydropyrazol-3-one (2.0 g, 4.29 mmole) was suspended in ethanol (17 ml) and water (1.85 ml). The brown slurry was treated with choline hydroxide (2.68 ml, 2.2 eq) (supplied as a 45% wt solution in methanol) at ambient temperature to form a deep purple solution which was stirred for 30 mins. The solution was filtered, and rinsed through with ethanol (4 ml). Triflouroacetic acid (0.36 ml, 1 eq) in water (1.85 ml) was added to the filtrate to form an orange-red slurry which was then heated to 78° C. (reflux) and stirred for 30 mins. The reaction was then cooled to 60° C. and treated with ethanol (25 ml, 12.5 vol) and stirred for a further 1 h at 60° C. The suspension was then cooled to ambient and stirred for 17 h. After filtration the cake was washed with ethanol (8 ml, 4 vol). The resulting solid was dried at 50° C. in vacuo to give 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline as an orange solid (2.02 g, 83%).

Proton NMR and IR data are consistent with the title compound.

EXAMPLE 3

Tablet Composition

Lactose, microcrystalline cellulose, sodium starch glycolate, magnesium stearate and 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline are blended in the proportions shown in Table 1 below. The blend is then compressed into tablets.

TABLE 1

| INGREDIENT | mg. |
|---|---|
| 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline | 8.45 |
| microcrystalline cellulose | 112 |
| lactose | 70 |
| sodium starch glycolate | 8 |
| magnesium stearate | 2 |

EXAMPLE 4

Injectable Parenteral Composition

An injectable form for administering 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline is produced by stirring 5.0 mg. of the compound in 1.0 ml. of normal saline.

While the preferred embodiments of the invention are illustrated by the above, it is to be understood that the invention is not limited to the precise instructions herein disclosed and that the right to all modifications coming within the scope of the following claims is reserved.

What is claimed is:

1. 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline.

2. A pharmaceutical composition comprising 2-(3,4-dimethylphenyl)-4-{[2-hydroxy-3'-(1H-tetrazol-5-yl)biphenyl-3-yl]-hydrazono}-5-methyl-2,4-dihydropyrazol-3-one choline and a pharmaceutically acceptable carrier or diluent.

3. A method of treating thrombocytopenia in a mammal in need thereof which comprises administering to such mammal a therapeutically effective amount of a compound as described in claim 1.

4. A method as claimed in claim 3, wherein the mammal is a human.

5. The method of claim 3 wherein the compound is administered orally.

6. The method of claim 3 wherein the compound is administered parenterally.

7. A process for preparing a pharmaceutical composition containing a pharmaceutically acceptable carrier or diluent and an effective amount of a compound as described in claim 1, which process comprises bringing the compound described in claim 1 into association with the pharmaceutically acceptable carrier or diluent.

8. The method of claim 3 further comprising co-administering a therapeutically effective amount of an agent selected from the group consisting of: a colony stimulating factor, cytokine, chemokine, interleukin or cytokine receptor agonist or antagonists, soluble receptors, receptor agonists and antagonist antibodies.

9. The method of claim 8 wherein the agent is selected from the group consisting of: G-CSF, GM-CSF, TPO, M-CSF, EPO, Gro-beta, IL-11, SCF, FLT3 ligand, LIF, IL-3, IL-6, IL-1, Progenipoietin, NESP, SD-01, IL-8, and IL-5.

10. A method of claim 3 wherein said thrombocytopenia is due to myelosuppression caused by chemotherapy or radiation therapy.

11. A method of claim 3 wherein said thrombocytopenia is due to an organ transplant.

12. A method of claim 3 wherein said thrombocytopenia is due to bone marrow, stem cell, or liver transplant.

13. A method of claim 3 wherein said thrombocytopenia is due to idiopathic thrombocytopenia purpura (ITP).

14. A method of claim 3 wherein said thrombocytopenia is due to myelodysplastic syndromes (MDS), aplastic anemia or leukemia.

15. A method of claim 3 wherein said thrombocytopenia is due to viral, fungal, microbial or parasitic infection.

16. A method of claim 3 wherein said thrombocytopenia is due to liver dysfunction.

17. A method of claim 3 wherein said thrombocytopenia is due to surgical procedures.

18. A method of claim 3 wherein said thrombocytopenia is drug—induced.

19. A process for preparing the compound of claim 1, which process comprises:
  i) dissolving 2-(3,4-dimethylphenyl)-4-{[2-hydroxy-3'-(1H-tetrazol-5-yl)biphenyl-3-yl]-hydrazono}-5-methyl-2,4-dihydropyrazol-3-one in an organic solvent or solvents, to form a solution;
  ii) adding one or more equivalents of choline hydroxide to the solution; and
  iii) isolating the prepared compound.

20. The process of claim 19 wherein the solution contains a mixture of ethyl acetate and ethanol.

21. The process of claim 19 wherein the solution contains tetrahydrofuran.

* * * * *